(12) United States Patent
Rehbein (10) Patent No.: US 11,337,601 B2
(45) Date of Patent: May 24, 2022

(54) PROBE DEVICE FOR A RESECTOSCOPE OR ANOTHER MICROINVASIVE INSTRUMENT (71) Applicant: Karl Storz SE & Co. KG, Tuttlingen (DE)

(72) Inventor: Stefan Rehbein, Immendingen-Hattingen (DE)

(73) Assignee: KARL STORZ SE & CO. KG, Tuttlingen (DE)

( * ) Notice: Subject to any disclaimer, the term of this patent is extended or adjusted under 35 U.S.C. 154(b) by 601 days.

(21) Appl. No.: 15/900,877

(22) Filed: Feb. 21, 2018

(65) Prior Publication Data

US 2018/0235455 A1  Aug. 23, 2018

(30) Foreign Application Priority Data

Feb. 21, 2017 (DE) .................. 10 2017 103 545.1

(51) Int. Cl.
*A61B 1/307* (2006.01)
*A61B 1/00* (2006.01)
(Continued)

(52) U.S. Cl.
CPC .......... *A61B 1/307* (2013.01); *A61B 1/00128* (2013.01); *A61B 1/018* (2013.01);
(Continued)

(58) Field of Classification Search
CPC ..... A61B 1/00128; A61B 1/018; A61B 1/307; A61B 1/00137; A61B 1/0016; A61B 18/14; A61B 2017/00367; A61B 2017/00407; A61B 2017/00486; A61B 17/28; A61M 39/10
See application file for complete search history.

(56) References Cited

U.S. PATENT DOCUMENTS 2,741,248 A * 4/1956 Woodhall ............... B23D 51/10
606/176
5,833,696 A * 11/1998 Whitfield ........... A61B 17/1285
606/143

(Continued)

FOREIGN PATENT DOCUMENTS

CN    105 250 023 A     1/2016
DE  10 2009 022 494 A1  11/2010

(Continued)

*Primary Examiner* — Aaron B Fairchild
(74) *Attorney, Agent, or Firm* — McGlew and Tuttle, P.C.

(57) ABSTRACT

A probe device (50), for a resectoscope (10) or another microinvasive instrument for working or manipulating tissue, includes a probe shaft (60) with a cylindrical portion (66) for arrangement in an instrument shaft (20) and with a distal end for arrangement near a distal end of the instrument shaft (20), an effecting device at the distal end of the probe shaft (60), and a sealing device (70) with a probe shaft channel (76) in which the cylindrical portion (66) of the probe shaft (60) is arranged. The probe shaft (60) is movable relative to the sealing device (70) parallel to the longitudinal axis of the probe shaft (60) and parallel to the longitudinal axis of the probe shaft channel (76). The sealing device (70) is formed from metal or ceramic or from another non-elastic material and is connected permanently to the probe shaft (60).

14 Claims, 4 Drawing Sheets (51) Int. Cl.
*A61B 1/018* (2006.01)
*A61B 17/3205* (2006.01)
*A61B 18/14* (2006.01)
*A61B 18/00* (2006.01)
*A61B 18/12* (2006.01)
*A61B 18/04* (2006.01)
*A61B 18/24* (2006.01)
*A61B 17/00* (2006.01)

(52) U.S. Cl.
CPC ......... *A61B 17/32056* (2013.01); *A61B 18/04* (2013.01); *A61B 18/12* (2013.01); *A61B 18/1485* (2013.01); *A61B 18/24* (2013.01); *A61B 2017/00345* (2013.01); *A61B 2018/0063* (2013.01); *A61B 2018/00172* (2013.01); *A61B 2018/00982* (2013.01); *A61B 2018/141* (2013.01); *A61B 2018/1407* (2013.01); *A61B 2018/1435* (2013.01)

(56) References Cited

U.S. PATENT DOCUMENTS

2003/0040737 A1* 2/2003 Merril .................... A61B 34/70
606/1
2006/0224120 A1 10/2006 Smith et al.
2011/0196403 A1* 8/2011 Robertson ........ A61B 17/22012
606/169

FOREIGN PATENT DOCUMENTS

DE  10 2011 079867 A1  1/2013
GB  2 335 858 A  10/1999
GB  2545559 A  *  6/2017  ......... A61B 18/1485

* cited by examiner

Fig. 3 III-III

Fig. 8 VIII-VIII

PROBE DEVICE FOR A RESECTOSCOPE OR ANOTHER MICROINVASIVE INSTRUMENT

CROSS REFERENCE TO RELATED APPLICATIONS

This application claims the benefit of priority under 35 U.S.C. § 119 of German Application 10 2017 103 545.1, filed Feb. 21, 2017, the entire contents of which are incorporated herein by reference.

FIELD OF THE INVENTION

The present invention relates to a probe device for a resectoscope or another microinvasive medical instrument for working or manipulating tissue, and to a microinvasive instrument having such a probe device.

BACKGROUND OF THE INVENTION

A resectoscope for transurethral resection or for gynecological or other uses comprises a resectoscope shaft, which can be inserted into the urethra, for example. The shaft of an endoscope and the shaft of a probe device are arranged in the resectoscope shaft. The shaft of the probe device can be moved in the resectoscope shaft by means of a device designated as a working element and located at the proximal end of the resectoscope shaft. At the distal end of the probe device, and therefore also in the region of the distal end of the resectoscope shaft, an effecting device is provided which can be moved relative to the distal end of the resectoscope shaft by means of the working element. The effecting device comprises, for example, one or more electrodes for monopolar or bipolar high-frequency surgery and electrocauterization of severed tissue. Alternatively, the effecting device can have, for example, a light exit surface through which the intensive light of a laser can emerge.

A resectoscope of this kind can generally be dismantled to a substantial extent in order to make complete cleaning easier, to be able to exchange a faulty component or to be able to adapt the resectoscope to the customary practice of the medical personnel or to the specific requirements of a medical procedure. In particular, the proximal end of the resectoscope shaft can generally be separated from the distal end of the working element, and the endoscope and the probe device can be removed from the resectoscope shaft, separated from the other components and exchanged. Moreover, during a medical intervention, the proximal end of the resectoscope shaft can be temporarily separated from the distal end of the working element, for example to drain off some of the flushing fluid that is used in the medical procedure.

Despite the substantial dismantlability and the mobility of the shaft of the probe in the resectoscope shaft, the proximal end of the resectoscope shaft has to be closed in a fluid-tight manner. For this purpose, a sealing device made of an elastic material is used in a conventional resectoscope. The sealing device comprises a channel for the shaft of the probe device, and a slit which reaches from the circumference as far as the channel and through which the shaft of the probe device can be inserted into the channel from the side. When the proximal end of the resectoscope shaft is connected to the distal end of the working element, the sealing device is compressed in the axial direction, such that the slit is closed and the sealing device bears on the shaft of the probe device and also on sealing faces at the proximal end of the resectoscope shaft and at the distal end of the working element.

A disadvantage of this arrangement is that force is needed to compress the sealing device when connecting the proximal end of the resectoscope shaft to the distal end of the working element. The patient may be injured by resulting accidental movements of the resectoscope shaft. A further disadvantage is that friction between the elastic sealing device and the shaft of the probe device offers resistance against a movement of the shaft of the probe device relative to the sealing device and therefore relative to the resectoscope shaft, which makes precision movement of the probe device difficult.

SUMMARY OF THE INVENTION

An object of the present invention is to make available an improved probe device for a resectoscope or for another microinvasive medical instrument for working or manipulating tissue and to make available an improved microinvasive medical instrument.

The reliable sealing action of the sealing device is conventionally dependent on the elasticity of the latter. Only this elasticity allows the probe shaft to be inserted from the side (i.e. in a radial direction) into the channel provided for this purpose in the sealing device through a slit. Embodiments of the present invention are based on the concept of providing, instead of an elastic sealing device, a sealing device that is made of a metal or of a ceramic or of another non-elastic material and of ensuring, in contrast to a conventional resectoscope, that the probe shaft can no longer be removed radially through a slit from the probe shaft channel in the sealing device.

A probe device for a resectoscope or another microinvasive medical instrument for working or manipulating tissue comprises a probe shaft with a cylindrical portion for arrangement in an instrument shaft and with a distal end for arrangement near a distal end of the instrument shaft, an effecting device at the distal end of the probe shaft, and a sealing device with a probe shaft channel in which the cylindrical portion of the probe shaft is arranged, wherein the probe shaft is movable relative to the sealing device parallel to the longitudinal axis of the probe shaft and parallel to the longitudinal axis of the probe shaft channel, wherein the sealing device is formed from metal or ceramic or from another non-elastic material and is connected permanently to the probe shaft.

The probe device is provided and configured in particular for a resectoscope for transurethral resection of diseased tissue from the bladder or prostate or for gynecological or other uses. The cylindrical and therefore also rectilinear portion of the probe shaft is in particular of a rigid configuration, in order to be able to take up not just tensile forces but also shear forces and to be able to transmit these to the effecting device. The cross-sectional surface area of the cylindrical portion of the probe shaft and the cross-sectional surface area of the probe shaft channel of the sealing device correspond substantially to each other. The cross-sectional surface area of the cylindrical portion of the probe shaft is in particular only slightly smaller than the cross-sectional surface area of the probe shaft channel, in order for the probe shaft to be guided in the probe shaft channel with little play and little friction. The cross-sectional surface area of the cylindrical portion of the probe shaft and the corresponding cross-sectional surface area of the probe shaft channel are in particular each circular. Alternatively, the cross-sectional surface area of the cylindrical portion of the probe shaft and the corresponding cross-sectional surface area of the probe shaft channel can each be non-circular, for example polygonal or elliptic.

The effecting device can comprise a high-frequency electrode for electrosurgical separation of tissue and/or for electrocauterization of separated tissue and/or a laser probe with a light exit surface for laser light. The probe device has in particular a greater cross-sectional surface area at the effecting device than at the cylindrical portion of the probe shaft. In particular, a high-frequency electrode (for example in the form of a loop) can have a width which is substantially greater than each linear dimension of the cross-sectional surface area of the cylindrical portion of the probe shaft.

The probe device can moreover have a clip or another guide device for form-fit guiding of the probe device on the shaft of an endoscope or on a tube in which the shaft of an endoscope can be arranged, or on another device acting as guide rail in an instrument shaft. This clip or other guide device is in particular arranged near the distal end of the probe device, between the effecting device and the cylindrical portion of the probe shaft. In the region of the clip or other guide device, the probe device has a greater cross section than in the cylindrical portion of the probe shaft.

In the proximal direction from the cylindrical portion, the probe device can moreover have a flexible lead for transmitting electrical or optical power. A plug connector for electrical and/or optical coupling to a power source can be provided at the proximal end of the flexible lead.

The non-elastic material of the sealing device is in particular non-elastic insofar as the sealing device is not deformed or not substantially deformed in the intended use. The elastic material of the sealing device has in particular an elastic modulus (E modulus) greater than 5 GPa or greater than 10 GPa or greater than 20 GPa or greater than 50 GPa, or a shear modulus (G modulus) greater than 1 GPa or greater than 5 GPa or greater than 10 GPa or greater than 20 GPa. The sealing device is in particular not formed from a rubber or a silicone rubber or elastomer or another elastomer.

The sealing device made of the non-elastic material is not deformed or not substantially deformed when connecting the proximal end of the instrument shaft to the distal end of the working element.

The inner surface of the probe shaft channel of the sealing device does not bear fully on the outer surface of the cylindrical portion of the probe shaft. Instead, a small annular gap remains between the outer surface of the cylindrical portion of the probe shaft and the inner surface of the probe shaft channel of the sealing device. However, on account of the non-elastic material of the sealing device and its resulting dimensional stability, this annular gap can be chosen to be so narrow that, on the one hand, the cylindrical portion of the probe shaft can move with minimal friction in the probe shaft channel of the sealing device and, on the other hand, only a very small amount of a flushing liquid or of another fluid can pass through the annular channel.

The probe shaft and the sealing device of the probe device are permanently connected to each other insofar as they cannot be separated from each other without destruction. The probe shaft cannot in particular be pulled completely out of the probe shaft channel of the sealing device, for example because, both in the distal direction and also in the proximal direction from its cylindrical portion, it has a cross section that is greater than the cross section of the probe shaft channel. In the distal direction, this greater cross section can be present, for example, at the effecting device and/or at the aforementioned clip or other guide device. In the proximal direction, this greater cross section can be present, for example, at a plug connector for the releasable mechanical and electrical and/or optical connection to a power source.

Since the sealing action of the sealing device made of the non-elastic material is not based on a compression and deformation of the sealing device, it is possible to design the probe device, the proximal end of the instrument shaft and the working element such that, when connecting the proximal end of the endoscope shaft to the distal end of the working element, no force is needed, or only a slight force is needed, particularly by comparison with the conventional sealing device made of an elastic material. There is therefore much less likelihood of an accidental movement of the instrument shaft, when opening and closing the connection to the working element, and therefore of possible injury to a patient.

In a probe device as described here, the sealing device is in particular not slit.

On account of the non-elastic material of the sealing device, a slit could not be closed by compression and elastic deformation of the sealing device. It is therefore not possible for the cylindrical portion of the probe shaft to be inserted into the probe shaft channel in the sealing device from the side. Instead, the sealing device remains connected permanently to the probe shaft.

In a probe device as described here, the sealing device moreover has in particular an endoscope shaft channel for receiving an endoscope shaft or for receiving a tube in which an endoscope shaft can be arranged.

The cross section of the endoscope shaft channel is adapted to the cross section of the tube for receiving an endoscope shaft, or to the cross section of an endoscope for which the microinvasive instrument and thus the probe device are provided, such that the endoscope shaft or the tube for receiving an endoscope shaft is guided with little play and little friction in the endoscope shaft channel of the sealing device and only a little liquid or another fluid can pass through a remaining annular channel.

In a probe device as described here, the endoscope shaft channel has in particular an annular extension in which a sealing element is arranged.

The sealing element is in particular configured as an O-ring made of Teflon, nitrile rubber, silicone rubber, silicone elastomer or another elastomer or another elastic material. The sealing element has in particular a toroidal shape or another annular shape with a circular, round or polygonal cross section.

In a probe device as described here, the sealing device has in particular a conical sealing face which is provided and configured to bear sealingly on a corresponding conical sealing face on an instrument shaft.

The diameter of the conical sealing face decreases in the distal direction in particular. Numerous conventional instrument shafts have a conical sealing face at their proximal ends. The probe device can be combined with such a conventional instrument shaft.

In a probe device as described here, the probe shaft channel has in particular an annular extension, in which a sealing element is arranged.

The sealing element is in particular configured as an O-ring made of Teflon, nitrile rubber, silicone rubber, silicone elastomer or another elastomer or another elastic material. The sealing element has in particular the shape of a toroid or of another ring with a circular, round or polygonal cross section. The sealing element can close the annular gap between the outer surface of the cylindrical portion of the probe shaft and the inner surface of the probe shaft channel of the sealing device and can thus further improve the sealing action.

Since the sealing element in the sealing device is not deformed when the proximal end of an instrument shaft is connected to the distal end of a working element, it also offers no resistance to this connection. Since the sealing element is also not pressed onto the outer surface of the cylindrical portion of the probe shaft, it also does not have to substantially increase the friction between the cylindrical portion of the probe shaft and the sealing device.

In a probe device as described here, the sealing device has in particular a coupling device for the releasable mechanical connection of the sealing device to the distal end of a working element of a resectoscope or of another microinvasive instrument.

The mechanical connection that the coupling device provides between the sealing device and the working element means that, when the proximal end of the instrument shaft is separated from the distal end of the working element, the sealing device does not remain at the proximal end of the instrument shaft. The mechanical connection that the coupling device provides between the sealing device and the working element can ensure that the sealing device instead remains at the distal end of the working element, from which it can then be separated manually.

In a probe device as described here, the sealing device in particular comprises an elastic latching device for forming a latched connection to the distal end of the working element of the resectoscope or of the other microinvasive instrument.

In a probe device as described here, the coupling device has in particular a groove or another recess for receiving an elastic latching element at the distal end of the working element of the resectoscope or of the other microinvasive instrument.

The latching device comprises, for example, a latching lug at one end of a flexurally elastic spar, which latching lug can engage in a groove or another recess at the distal end of the working element. The latching action can be adjusted via the elastic properties of the elastic spar or of the other elastic latching device, such that the sealing device remains securely on the working element when separating the instrument shaft from the working element, but can then be easily separated manually from the working element.

In a probe device as described here, the sealing device comprises a catch or an L-shaped groove for forming a bayonet connection to the distal end of the working element of the resectoscope or of the other microinvasive instrument.

In order to produce and release a bayonet connection between the sealing device and the distal end of the working element of the microinvasive instrument, the distal end of the working element is in particular configured such that the probe shaft and optionally an endoscope shaft, which are guided with little play in the sealing device, can be moved along arc-shaped trajectories relative to the distal end of the working element.

A microinvasive medical instrument for working or manipulating tissue comprises an instrument shaft with a distal end and a proximal end, a working element for releasable connection to the proximal end of the instrument shaft and for releasable connection to a proximal end of an endoscope and for releasable connection to a proximal end of a probe shaft and for manual movement of the probe shaft relative to the instrument shaft, wherein a space for receiving the sealing device of a probe device according to one of the preceding claims is provided between the distal end of the working element and the proximal end of the instrument shaft.

For this purpose, the distal end of the working element has in particular features that correspond to described features of the probe device, in particular of the sealing device.

In a microinvasive instrument as described here, a conical sealing face is provided in particular at the proximal end of the instrument shaft and corresponds at least partially to a conical sealing face of a sealing device of a probe device as described here.

The conical sealing face at the proximal end of the instrument shaft in particular does not correspond to or only partially corresponds to a conical face on the working element. Part of the conical sealing face at the proximal end of the instrument shaft or the entire conical sealing face at the proximal end of the instrument shaft corresponds to a conical sealing face of a sealing device of a probe device as described here.

In a microinvasive instrument as described here, an opening for the probe shaft or for the endoscope shaft is provided in particular at the distal end of the working element, wherein the opening for the probe shaft or for the endoscope shaft has a cross section which permits a movement of the probe shaft or of the endoscope shaft in the opening during a rotation of the sealing device relative to the distal end of the working element.

The opening has in particular a cross section which is obtained by moving the cross section of the probe shaft or of the endoscope shaft along a circular arc portion whose center point lies on the axis about which the sealing device is to rotate upon production or release of a bayonet connection to the distal end of the working element.

The microinvasive instrument is in particular a resectoscope.

The present invention is described in detail below with reference to the attached figures. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
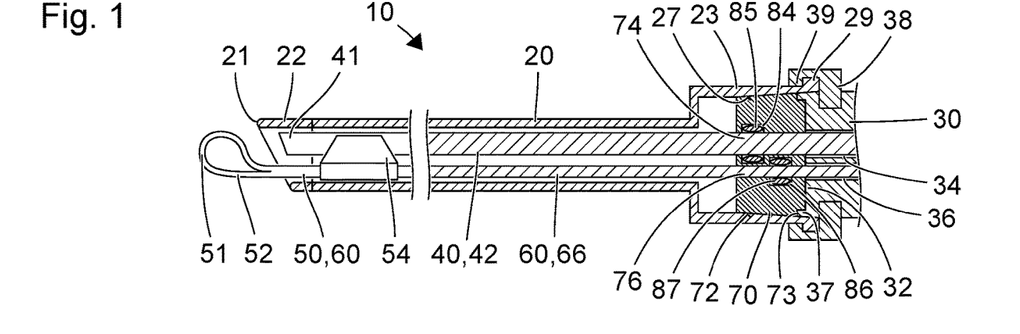
FIG. 1 is a schematic longitudinal sectional view through a part of a resectoscope.

Referring to the drawings, FIG. 1 shows a schematic view of a longitudinal section through a central region and through the distal end (on the left in FIG. 1) of a resectoscope 10 as an example of a microinvasive instrument, in which an effecting device is movable relative to a shaft in order to work or manipulate tissue. The distal end of the resectoscope 10 is shown only partially in the section.

The resectoscope 10 comprises a substantially tubular resectoscope shaft 20 with a distal end 21 and a proximal end 23. The distal end 21 of the resectoscope shaft 20 is formed by a portion 22 made of an electrically insulating material. At its proximal end 23, the resectoscope shaft 20 is widened in a cup shape and has a conical sealing face 27 on its inner side. Two or more catches 29 are provided on the farthest proximal edge of the resectoscope shaft 20 and protrude radially outward.

The resectoscope 10 moreover comprises a working element 30, of which only the distal end 32 can be seen in FIG. 1, said distal end 32 being mechanically connected to the proximal end 23 of the resectoscope shaft 20.

The resectoscope 10 moreover comprises an endoscope 40, of which only an endoscope shaft 42 can be seen in FIG. 1. The endoscope shaft 42 is arranged for the most part inside the resectoscope shaft 20. The distal end 41 of the endoscope 40 is arranged in or near the distal end 21 of the resectoscope shaft 20. The distal region of the endoscope shaft 42 is not shown in the section, in contrast to the rest of the endoscope shaft 42 and other components of the resectoscope 10.

The resectoscope 10 moreover comprises a probe device 50, of which only a distal end 51 and part of a probe shaft 60 can be seen in FIG. 1. The probe shaft 60 is arranged for the most part inside the resectoscope shaft 20. The probe shaft 60 comprises a cylindrical portion 66 which extends over much of the length of the resectoscope shaft 20. The distal region of the probe shaft 60 is not shown in the section, in contrast to the cylindrical portion 66 of the probe shaft 60.

In the example shown, the distal end 51 of the probe device 50 is formed by a coil-shaped or loop-shaped electrode 52 for electrosurgical uses as effecting device. The electrode 52 has dimensions which go considerably beyond the cross section of the cylindrical portion 66 of the probe shaft 60. Alternatively or additionally, at the distal end 51 of the probe device as effecting device, it is possible to provide a light exit face of a fiber optic guide through which intensive laser light can emerge to permit cutting, ablation or obliteration of tissue.

In the example shown, the probe device 50 moreover has a guide device 54. The guide device 54 has the shape of a clip which is rigidly connected to the probe shaft 60 and engages more than half way round the endoscope shaft 42. The guide device 54 is guided with form-fit engagement on the endoscope shaft 42, such that although the probe device 50 can be moved relative to the endoscope shaft 42 parallel to the longitudinal axis of the endoscope shaft 42, it can only be moved to a limited extent, if at all, in other directions. In a departure from the view shown in FIG. 1, the guide device 54 can engage all the way round the endoscope shaft 42. The dimensions of the guide device 54 also go considerably beyond the cross section of the cylindrical portion 66 of the probe shaft 60.

The endoscope shaft 42 and the probe shaft 60 extend along substantially the entire length of the resectoscope shaft 20. The cross section of the resectoscope shaft 20 is configured such that the resectoscope shaft 20 can receive the endoscope shaft 42 and the probe shaft 60 and, moreover, a flushing liquid or another fluid can be conveyed through the resectoscope shaft 20.

A first opening 34 in the shape of a cylindrical through-channel for the endoscope shaft 42 and a second opening 36 in the shape of a cylindrical through-channel for the cylindrical portion 66 of the probe shaft 60 of the probe device 50 are provided in the distal end 32 of the working element 30. Both openings 34, 36 extend parallel to each other and parallel to the longitudinal axis of the resectoscope shaft 20. Moreover, there is an annular collar 37 at the distal end 32 of the working element 30.

A coupling ring 38 with two or more catches 39 is moveover provided at the distal end 32 of the working element 30. The coupling ring 38 is rotatable about a rotation axis in the drawing plane of FIG. 1. The catches 39 on the coupling ring 38 correspond to the catches 29 at the proximal end 23 of the resectoscope shaft 20. In the configuration shown in FIG. 1, the catches 39 on the coupling ring 38 engage behind the catches 29 at the proximal end 23 of the resectoscope shaft 20, such that the proximal end 23 of the resectoscope shaft 20 is held with form-fit engagement on the distal end 32 of the working element 30. This connection can be released by rotation of the coupling ring 38. Thus, a bayonet connection formed by the catches 29 at the proximal end 23 of the resectoscope shaft 20 and by the catches 39 on the coupling ring 38 is present between the proximal end 23 of the resectoscope shaft 20 and the distal end 32 of the working element 30.

The sealing device 70 has a conical sealing face 72 whose diameter decreases in the distal direction (to the left in FIG. 1) and which corresponds to the conical sealing face 27 at the proximal end 23 of the resectoscope shaft 20. Moreover, the sealing device has an annular step 73, which corresponds to the annular collar 37 at the distal end 32 of the working element 30. The form-fit engagement of the collar 37 at the distal end 32 of the working element in the step 73 at the sealing device 70, as shown in FIG. 1, results in correct positioning of the sealing device 70 relative to the distal end 32 of the working element 30.

The resectoscope 10 moreover comprises a sealing device 70. The sealing device 70 has an endoscope shaft channel 74 for receiving the endoscope shaft 42 and a probe shaft channel 76 for receiving the cylindrical portion 66 of the probe shaft 60. The cross section of the endoscope shaft channel 74 is adapted to the cross section of the endoscope shaft 42 such that only a small annular gap remains between the inner surface of the endoscope shaft channel 74 and the outer surface of the endoscope shaft 42 and such that the endoscope shaft 42 is guided in the endoscope shaft channel 74 with little play and little friction. The cross section of the probe shaft channel 76 is adapted to the cross section of the cylindrical portion 66 of the probe shaft 60 such that only a narrow annular gap remains between the inner surface of the probe shaft channel 76 of the sealing device 70 and the outer surface of the cylindrical portion 66 of the probe shaft 60 and such that the cylindrical portion 66 of the probe shaft 60 is guided in the probe shaft channel 76 with little play and little friction.

The sealing device 70 is formed from a metal, a ceramic or another non-elastic material and is not deformed, or not substantially deformed, in the intended use in the resectoscope 10. The low elasticity of the sealing device permits precise adherence to the intended geometries of the annular gap around the endoscope shaft 42 in the endoscope shaft channel 74 and of the intended gap around the cylindrical portion 66 of the probe shaft 60 in the probe shaft channel 76. Both annular gaps can therefore be made so narrow that only a little fluid can pass through the annular gaps.

In the example shown in FIG. 1, an annular groove 84 is additionally provided in the endoscope shaft channel 74 and locally increases the cross section of the endoscope shaft channel. An O-ring 85 made of Teflon, nitrile rubber, silicone rubber, silicone elastomer or another elastomer or another elastic material is arranged in the annular groove 84 in the endoscope shaft channel 74. The O-ring 85 is so dimensioned, and the elastic properties of the O-ring 85 so chosen, that it closes the annular gap between the outer surface of the endoscope shaft 42 and the inner surface of the endoscope shaft channel 74 elastically and in a fluid-tight manner.

In the example shown in FIG. 1, an annular groove 86 is moreover provided in the probe shaft channel 76 and locally increases the cross section of the probe shaft channel 76. An O-ring 87 made of Teflon, nitrile rubber, silicone rubber, silicone elastomer or another elastomer or another elastic material is arranged in the annular groove 86 in the probe shaft channel 76. The O-ring 87 is so dimensioned, and the elastic properties of the O-ring 87 so chosen, that the O-ring 87 bears on the outer surface of the cylindrical portion 66 of the probe shaft 60 and closes the annular gap between the outer surface of the cylindrical portion 66 of the probe shaft 60 and the inner surface of the probe shaft channel 76 elastically and in a fluid-tight manner.

When the resectoscope 10 is being dismantled, the endoscope shaft 42 is pulled in the proximal direction (to the right in FIG. 1) out of the resectoscope shaft 20, the sealing device 70 and the working element 30. This is possible because the endoscope shaft 42 has a continuously cylindrical shape. In contrast to the endoscope shaft 42, the probe device 50 has, at or near its distal end 51, a cross section that is considerably greater compared to the cylindrical portion 66 of the probe shaft 60, this on account of a guide device 54 and/or an effecting device 52. Removal of the probe shaft 60 in the proximal direction is thus ruled out. In contrast to a conventional sealing device made of an elastic material, the sealing device 70 remains on the probe shaft 60 and thus forms with the latter a unit that cannot be separated without being destroyed.

Near its distal end 32, the working element 30 has a slit (not shown in FIG. 1) which extends from an outer circumference of the working element 30 to the second opening 36 and allows the cylindrical portion 66 of the probe shaft 60 to be inserted into the working element 30 from the side.

Figure 2:
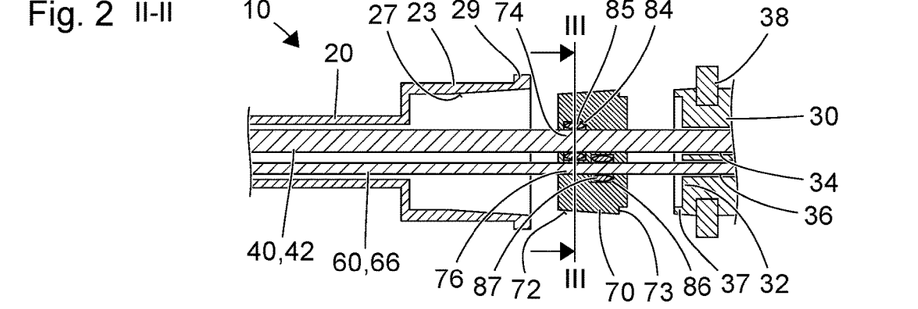
FIG. 2 is a schematic longitudinal sectional view through the resectoscope from FIG. 1 in another configuration.

FIG. 2 shows a further schematic view of a longitudinal section through the central region of the resectoscope 10 from FIG. 1. The section plane II-II of FIG. 2 corresponds to the section plane of FIG. 1. The view in FIG. 2 differs from the view in FIG. 1 in that another configuration is shown. The configuration shown in FIG. 2 is present, for example, when assembling or dismantling the resectoscope 10.

Proceeding from the configuration shown in FIG. 1, the configuration shown in FIG. 2 arises when the coupling ring 38 is rotated such that the catches 39 on the coupling ring 38 are removed from the catches 29 at the proximal end 23 of the resectoscope shaft 20 and the bayonet connection between the proximal end 23 of the resectoscope shaft 20 and the distal end 32 of the working element 30 is separated. Thereafter, the resectoscope shaft 20 and the sealing device 70 can be moved in the distal direction relative to the working element 30, for example as far as the positions shown in FIG. 2.

Proceeding from the configuration shown in FIG. 2, the resectoscope shaft 20 can be pulled off in the distal direction, the endoscope shaft 42 can be pulled out in the proximal direction, and then the cylindrical portion 66 of the probe shaft 60 can be removed from the working element 30, for example in a movement orthogonal to the drawing plane of FIG. 2, through a slit (not shown in FIG. 2) in the working element 30. As has been mentioned, the cylindrical portion 66 of the probe shaft 60 remains in the probe shaft channel 76 of the sealing device.

Figure 3:
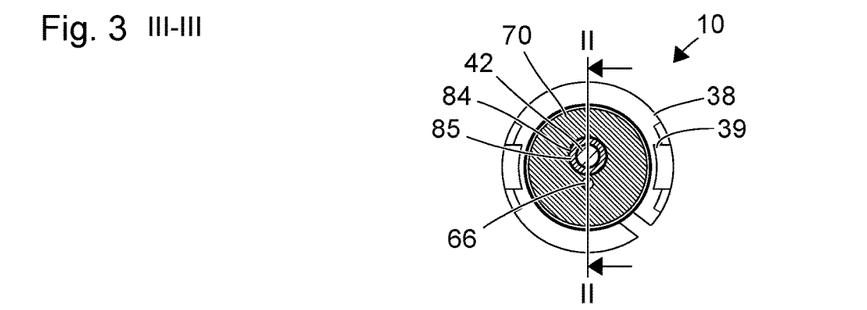
FIG. 3 is a schematic cross sectional view through the resectoscope from FIGS. 1 and 2.

FIG. 3 shows a schematic view of a further section through the resectoscope 10 from FIGS. 1 and 2, in the configuration shown in FIG. 2. The section plane III-III of FIG. 3 is orthogonal to the section plane II-II of FIG. 2. The position of the section plane II-II of FIG. 2 is indicated in FIG. 3. The section plane III-III of FIG. 3 is indicated in FIG. 2.

The section plane III-III of FIG. 3 cuts through only the sealing device 70, specifically in the region of the annular groove 84 in the endoscope shaft channel 74 and of the O-ring 85 in the annular groove 84. To simplify matters, the cross sections of the endoscope shaft 42 and of the cylindrical portion 66 of the probe shaft 60 are indicated as homogenous hatched surface areas in FIG. 3. The catches 39 on the coupling ring 38 at the distal end 32 of the working element 30 (cf. FIGS. 1 and 2) can also be seen in FIG. 3. The coupling ring has a slit whose function will become clear from FIGS. 9 and 12.

Unlike conventional sealing devices for resectoscopes, the sealing device 70 does not have a slit through which the cylindrical portion 66 of the probe shaft 60 could be inserted into the sealing device 70 from the side. Therefore, no compression and no elastic deformation of the sealing device 70 is needed in order to reliably close such a slit. The sealing device 70 can therefore be formed from a metal, a ceramic or another non-elastic material. On the other hand, if the probe shaft 60 has an enlarged cross section at its distal end (as shown in FIGS. 1 and 2), the sealing device 70 has to remain on the cylindrical portion 66 of the probe shaft 60. The probe shaft 60 and the sealing device 70 therefore form a unit that cannot be separated without destruction.

In a departure from the view in FIGS. 1 to 3, the sealing device can only have either an annular groove 84 in the endoscope shaft channel 74 and an O-ring 85 in the annular groove 84 or an annular groove 86 in the probe shaft channel 76 and an O-ring 87 in the annular groove 86.

Figure 4:
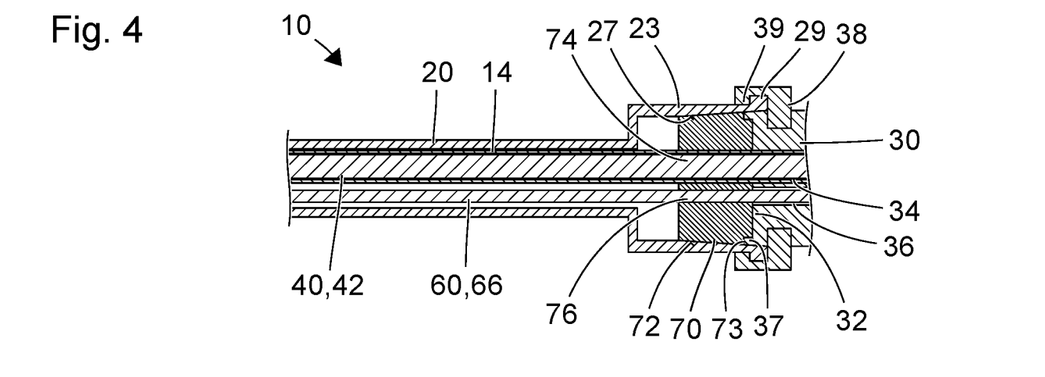
FIG. 4 is a schematic longitudinal sectional view through a part of a resectoscope.

FIG. 4 shows a schematic view of a longitudinal section through a central region of a further resectoscope 10 which, in terms of certain features, properties and functions, is similar to the resectoscope shown in FIGS. 1 to 3, particularly also in respect of the distal end of the resectoscope 10 not shown in FIG. 4. The section plane of FIG. 4 corresponds to the section planes of FIGS. 1 and 2. The configuration shown in FIG. 4 corresponds to the configuration shown in FIG. 1. Features, properties and functions that distinguish the resectoscope shown in FIG. 4 from the resectoscope shown in FIGS. 1 to 3 are in particular described below.

The resectoscope 10 shown in FIG. 4 differs from the resectoscope shown in FIGS. 1 to 3 particularly in that it comprises a guide tube 14 for the endoscope shaft 42.

The resectoscope 10 shown in FIG. 4 moreover differs from the resectoscope shown in FIGS. 1 to 3 in that no annular grooves or O-rings are provided either in the endoscope shaft channel 74 or in the probe shaft channel 76 of the sealing device 70. The sealing action of the sealing device 70 is thus based solely on the small widths of the annular gaps around the cylindrical portion 66 of the probe shaft 60 and around the endoscope shaft 42 of the endoscope 40 or around the guide tube 14.

Figure 5:
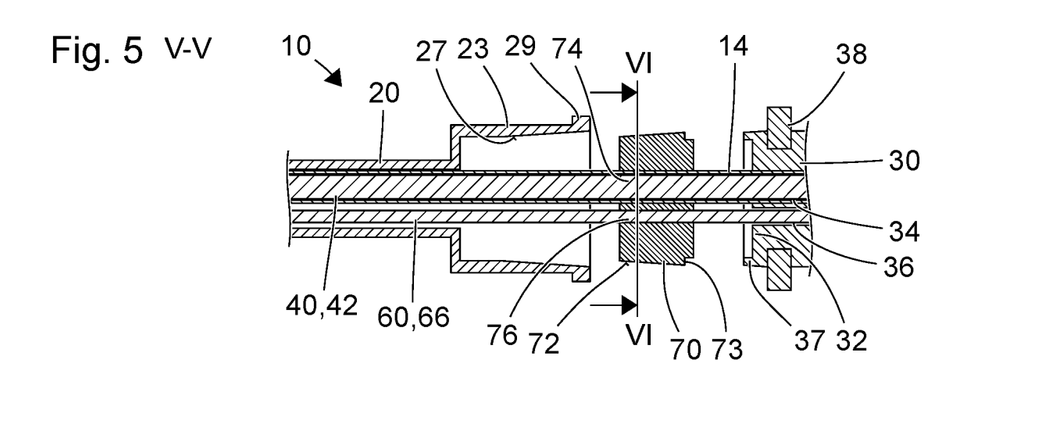
FIG. 5 is a schematic longitudinal sectional view through the resectoscope from FIG. 4 in another configuration.

FIG. 5 shows a schematic view of a further section through the resectoscope 10 shown in FIG. 4. The section plane V-V of FIG. 5 corresponds to the section plane of FIG. 4. The configuration shown in FIG. 5 corresponds to the configuration shown in FIG. 2.

The guide tube 14 can be rigidly and permanently connected either to the resectoscope shaft 20 or to the sealing device 70 or to the working element 30.

Figure 6:
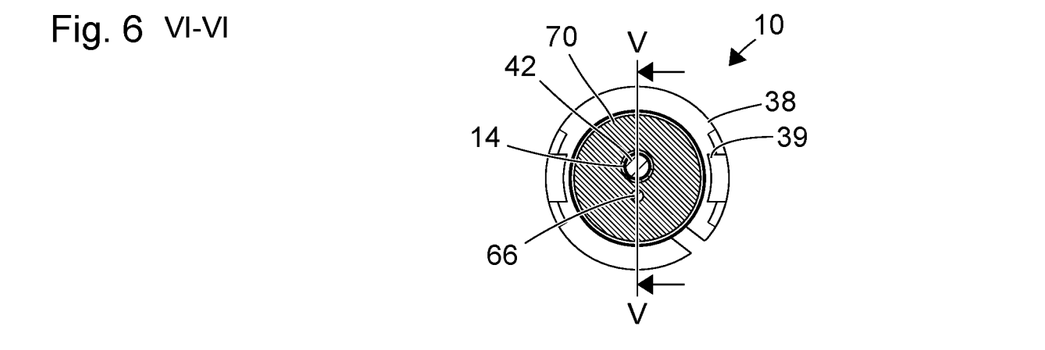
FIG. 6 is a schematic cross sectional view through the resectoscope from FIGS. 4 and 5.

FIG. 6 shows a schematic view of a further section through the resectoscope 10 shown in FIGS. 4 and 5. The section plane VI-VI of FIG. 6 is orthogonal to the section plane V-V of FIG. 5. The position of the section plane VI-VI of FIG. 6 is indicated in FIG. 5. The position of the section plane V-V of FIG. 5 is indicated in FIG. 6.

The features of the resectoscope shown in FIGS. 1 to 3 and of the resectoscope shown in FIGS. 4 to 6 can be combined with one another. In particular, a guide tube 14 as shown in FIGS. 4 to 6 can also be provided in the resectoscope shown in FIGS. 1 to 3. The O-ring 85 in the annular groove 84 in the endoscope shaft channel 74 bears in particular on the outer surface of the guide tube 14.

Moreover, in the resectoscope shown in FIGS. 1 to 3, in the same way as in the resectoscope shown in FIGS. 4 to 6, it is possible to dispense with the annular groove 84 in the endoscope shaft channel 74 and the O-ring 85 in the annular groove 84 and/or with the annular groove 86 in the probe shaft channel 76 and the O-ring 87 in the annular groove 86.

Figure 7:
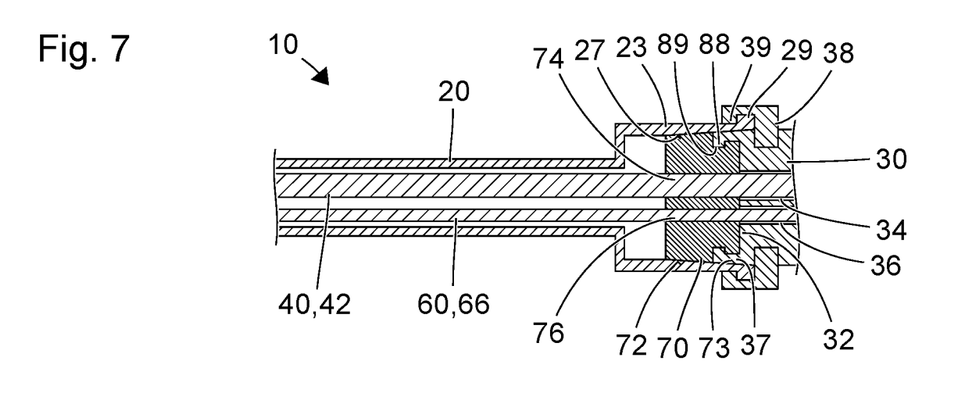
FIG. 7 is a schematic longitudinal sectional view through a part of a further resectoscope.

FIG. 7 shows a schematic view of a longitudinal section through a central region of a further resectoscope 10 which, in terms of certain features, properties and functions, is similar to the resectoscopes shown in FIGS. 1 to 6, particularly also in respect of the distal end of the resectoscope 10 not shown in FIG. 7. The section plane of FIG. 7 corresponds to the section planes of FIGS. 1, 2, 4 and 5. The configuration shown in FIG. 7 corresponds to the configurations shown in FIGS. 1 and 4. Features, properties and functions that distinguish the resectoscope shown in FIG. 7 from the resectoscopes shown in FIGS. 1 to 6 are in particular described below.

The resectoscope 10 shown in FIG. 7 differs from the resectoscopes shown in FIGS. 1 to 6 particularly in that the sealing device 70 is connected to the distal end 32 of the working element 30 by a bayonet connection. At the distal end 32 of the working element 30, two or more catches 88 are provided instead of an annular collar 37 or, in a departure from the example shown here, in addition to this annular collar 37. A corresponding number of corresponding and in each case L-shaped grooves 89 are provided on the sealing device 70. Each L-shaped groove 89 has an axial portion parallel to the longitudinal axes of the resectoscope shaft 20, the endoscope shaft 42 and the cylindrical portion 66 of the probe shaft, and a portion extending in the circumferential direction. In the configuration shown in FIG. 7, the catches 88 at the distal end 32 of the working element 30 engage in the circumferentially extending portions of the L-shaped grooves 89 on the sealing device 70 and thus produce a form-fit connection between the distal end 32 of the working element 30 and the sealing device 70.

Figure 8:
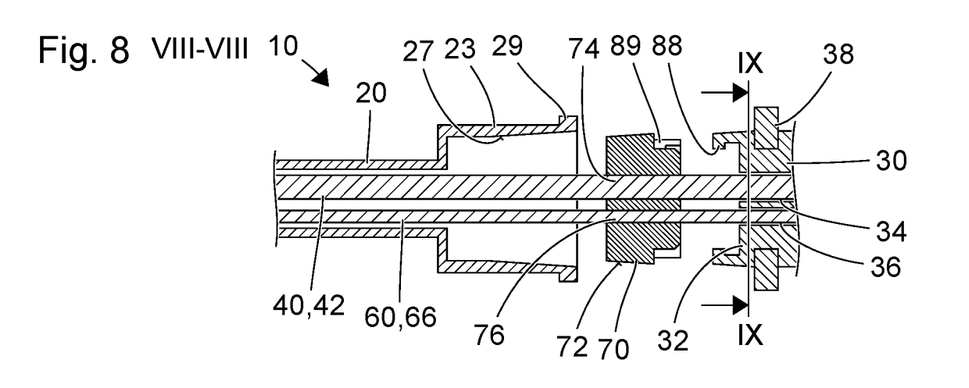
FIG. 8 is a schematic longitudinal sectional view through the resectoscope from FIG. 7 in another configuration.

FIG. 8 shows a further schematic view of a section through the resectoscope 10 from FIG. 7. The section plane VIII-VIII of FIG. 8 corresponds to the section plane of FIG. 7 and to the section planes of FIGS. 1, 2, 4 and 5. The configuration shown in FIG. 8 corresponds to the configurations shown in FIGS. 2 and 5.

In the arrangement of the sealing device 70 shown in FIG. 8, the L-shaped grooves 89 on the sealing device 70 can be seen spaced apart from the distal end 32 of the working element 30. Proceeding from the configuration shown in FIG. 7, the configuration shown in FIG. 8 can be reached by first rotating the sealing device 70 relative to the distal end 32 of the working element 30 about a predetermined angle in order to move the catches 88 at the distal end 32 of the working element 30 into the transition region between the circumferential portions and the axial portions of the L-shaped grooves 89 on the sealing device 70. Thereafter, the sealing device 70 can be separated in the axial direction from the distal end 32 of the working element 30.

Figure 9:
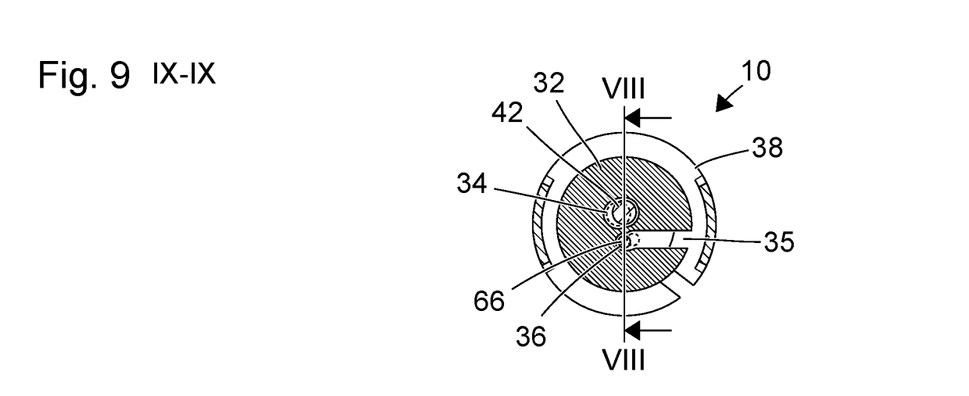
FIG. 9 is a schematic cross sectional view through the resectoscope from FIGS. 7 and 8.

FIG. 9 shows a further schematic view of a section through the resectoscope 10 from FIGS. 7 and 8. The section plane IX-IX of FIG. 8 is orthogonal to the section plane VIII-VIII of FIG. 8 and parallel to the section planes of FIGS. 3 and 6. The position of the section plane VIII-VIII of FIG. 8 is indicated in FIG. 9. The position of the section plane IX-IX of FIG. 9 is indicated in FIG. 8.

In contrast to the section plane III-III of FIG. 3 and the section plane VI-VI of FIG. 6, the section plane IX-IX of FIG. 9 does not cut through the sealing device 70 but instead the distal end 32 of the working element 30.

The aforementioned slit 35 in the working element 30 can be seen in FIG. 9, said slit 35 permitting lateral insertion of the cylindrical portion 66 of the probe shaft 60 into the second opening 36 in the distal end 32 of the working element 30. The slit 35 reaches from a circumference of the distal end 32 of the working element 30 as far as the second opening 36 formed as a through-channel. In order to insert the cylindrical portion 66 of the probe shaft 60 into the second opening 36 or to remove the cylindrical portion 66 of the probe shaft 60 from the second opening 36 with a movement in a direction parallel to the section plane IX-IX of FIG. 9, the coupling ring 38 can be brought to a position in which a slit in the coupling ring 38 is congruent with the slit 35 in the distal end 32 of the working element 30.

It can also be see from FIG. 9 that, in the resectoscope 10 shown in FIGS. 7 to 9, both the first opening 34 and also the second opening 36 in the distal end 32 of the working element 30 are slightly greater than the cross sections of the endoscope shaft 42 and of the cylindrical portion 66 of the probe shaft 60, respectively, such that the sealing device 70, together with the endoscope shaft 42 and the cylindrical portion 66 of the probe shaft 60 which are guided with little play in the endoscope shaft channel 74 and in the probe shaft channel 76 of the sealing device 70 (cf. FIGS. 7 and 8), can be rotated relative to the distal end 32 of the working element 30 about a predetermined angle in order to form or release the bayonet connection (shown in FIGS. 7 and 8) between the sealing device 70 and the distal end 32 of the working element 30. Positions that the cross sections of the endoscope shaft 42 and of the probe shaft 66 can reach during this rotation movement are indicated by broken lines in FIG. 9.

Figure 10:
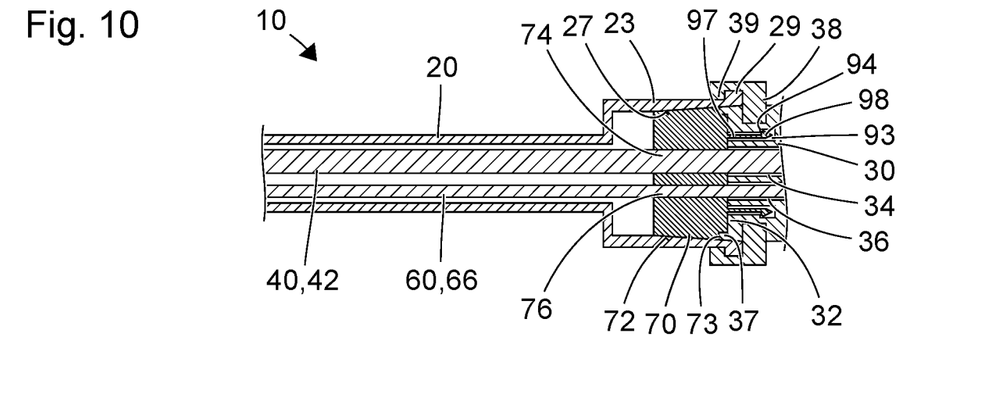
FIG. 10 is a schematic longitudinal sectional view through a part of a further resectoscope.

FIG. 10 shows a schematic view of a longitudinal section through a further resectoscope 10 which, in terms of certain features, properties and functions, is similar to the resectoscopes shown in FIGS. 1 to 9. The section plane of FIG. 10 corresponds to the section planes of FIGS. 1, 2, 4, 5, 7 and 8. The configuration shown in FIG. 10 corresponds to the configurations shown in FIGS. 1, 4 and 7. Features, properties and functions that distinguish the resectoscope shown in FIG. 10 from the resectoscopes shown in FIGS. 1 to 9 are in particular described below.

The resectoscope shown in FIG. 10 differs from the resectoscopes shown in FIGS. 1 to 9 particularly in that recesses 93 with steps 94 are provided at the distal end 32 of the working element 30, in which flexurally elastic spars 97 on the sealing device 70 engage. Latching lugs 98 are provided at the free ends of the flexurally elastic spars 97 of the sealing device 70 and, in the configuration shown in FIG. 10, engage behind the steps 94 in the recesses 93 and thus hold the sealing device 70 with form-fit engagement on the distal end 32 of the working element 30.

Figure 11:
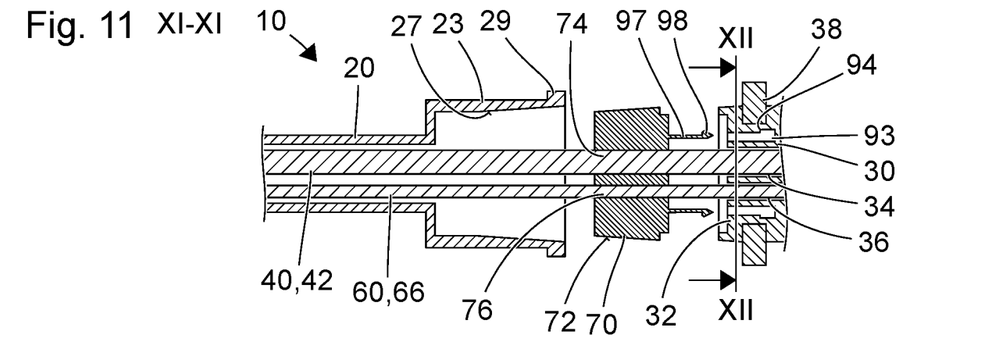
FIG. 11 is a schematic longitudinal sectional view through the resectoscope from FIG. 10 in a further configuration.

FIG. 11 shows a further schematic view of a section through the resectoscope 10 shown in FIG. 10. The section plane XI-XI of FIG. 11 corresponds to the section plane of FIG. 10 and to the section planes of FIGS. 1, 2, 4, 5, 7 and 8. The configuration shown in FIG. 11 corresponds to the configurations shown in FIGS. 2, 5 and 8.

Proceeding from the configuration shown in FIG. 10, the movement of the sealing device 70 to the position (shown in FIG. 11) relative to the distal end 32 of the working element 30 initially requires an excursion of the latching lugs 98 and therefore an elastic deformation of the flexurally elastic spars 97 counter to their elastic restoring force. Manual removal of the sealing device 70 from the distal end 32 of the working element 30 therefore requires a predetermined force, which is dependent on the exact geometry of the steps 94, the latching lugs 98 and the flexurally elastic spars 97 and on the elastic properties of the material from which the flexurally elastic spars 97 are formed. The predetermined force is in particular set in such away that, upon separation of the proximal end 23 of the resectoscope shaft 20 from the distal end 32 of the working element 30, it is ensured with sufficient certainty that the sealing device 70 does not remain on the proximal end 23 of the resectoscope shaft 20, and moreover that the sealing device 70 can then be separated sufficiently easily from the distal end 32 of the working element 30.

Figure 12:
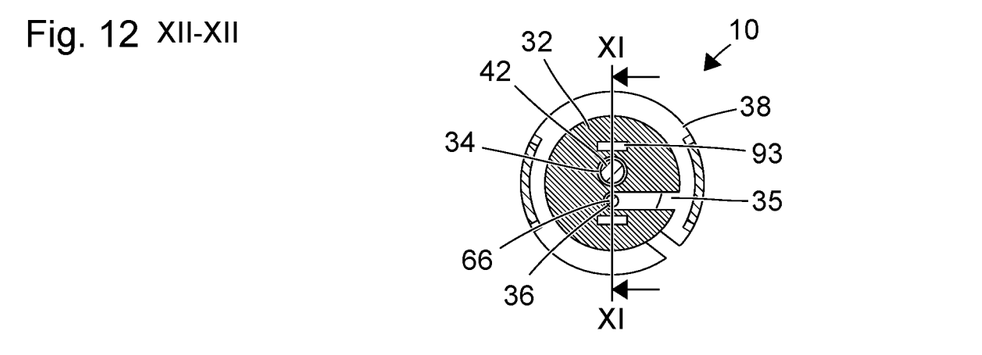
FIG. 12 is a schematic cross sectional view through the resectoscope from FIGS. 10 and 11.

FIG. 12 shows a schematic view of am further section through the resectoscope 10 from FIGS. 10 and 11. The section plane XII-XII of FIG. 12 is orthogonal to the section plane XI-XI of FIG. 11 and corresponds to the section plane IX-IX of FIG. 9. The position of the section plane XII-XII of FIG. 12 is indicated in FIG. 11. The position of the section plane XI-XI of FIG. 11 is indicated in FIG. 12.

In the example shown, the recesses 93 at the distal end 32 of the working element 30 are each pocket-shaped with rectangular cross sections.

While specific embodiments of the invention have been shown and described in detail to illustrate the application of the principles of the invention, it will be understood that the invention may be embodied otherwise without departing from such principles.

The invention claimed is:

1. A probe device for a resectoscope or another microinvasive medical instrument for working or manipulating tissue, the probe device comprising:
   an instrument shaft;
   a probe shaft with a cylindrical portion for arrangement in the instrument shaft and with a distal end for arrangement near a distal end of the instrument shaft;
   an effecting device at the distal end of the probe shaft; and
   a sealing device with a probe shaft channel in which the cylindrical portion of the probe shaft is arranged, wherein the probe shaft is movable relative to the sealing device in a direction parallel to a longitudinal axis of the probe shaft and parallel to a longitudinal axis of the probe shaft channel,
   wherein the sealing device has a conical sealing face which is provided and configured to bear sealingly on a corresponding conical sealing face on the instrument shaft, the sealing device being configured to seal an interior portion of the instrument shaft.

2. The probe device according to claim 1, wherein the probe shaft channel has an annular recess, in which a sealing element is arranged.

3. The probe device according to claim 1, wherein the sealing device has a coupling device for a releasable mechanical connection of the sealing device to the distal end of a working element of a resectoscope or of another microinvasive instrument.

4. The probe device according to claim 3, wherein the sealing device comprises an elastic latching device for forming a latched connection to the distal end of the working element of the resectoscope or of the other microinvasive instrument.

5. The probe device according to claim 3, wherein the coupling device has a groove or another recess for receiving an elastic latching element at the distal end of the working element of the resectoscope or of the other microinvasive instrument.

6. The probe device according to claim 3, wherein the sealing device comprises a catch or an L-shaped groove for forming a bayonet connection to the distal end of the working element of the resectoscope or of the other microinvasive instrument.

7. The probe device according to claim 1, wherein the sealing device is configured to be arranged radially inward of an annular portion of the instrument shaft defining a portion of an interior space.

8. The probe device according to claim 1, wherein the material is one of metal and ceramic.

9. A probe device for a resectoscope or another microinvasive medical instrument for working or manipulating tissue, the probe device comprising:
   an instrument shaft;
   a probe shaft with a cylindrical portion configured to be arranged in an interior space of the instrument shaft and with a distal end for arrangement adjacent a distal end of the instrument shaft;
   an effecting device at the distal end of the probe shaft; and
   a sealing device with a probe shaft channel in which the cylindrical portion of the probe shaft is arranged, wherein the probe shaft is movable relative to the sealing device in a direction parallel to a longitudinal axis of the probe shaft and parallel to a longitudinal axis of the probe shaft channel, having a conical sealing face which is provided and configured to bear sealingly on a corresponding conical sealing face on the instrument shaft, the sealing device being configured to seal an interior portion of the instrument shaft.

10. The probe device according to claim 9, wherein the sealing device is configured to be arranged radially inward of an annular portion of the instrument shaft defining a portion of the interior space in the proximal end of the instrument shaft.

11. The probe device according to claim 9, wherein the sealing device has a coupling device for a releasable mechanical connection of the sealing device to the distal end of a working element of a resectoscope or of another microinvasive instrument.

12. The probe device according to claim 9, wherein the material is one of metal and ceramic.

13. The probe device according to claim 9, wherein the cylindrical portion of the probe shaft is configured to be guided via a guide device located in the interior space between the sealing device and the distal end of the probe shaft.

14. The probe device according to claim 9, wherein the sealing device comprises at least one groove in which a sealing element is arranged, the sealing element being in contact with the cylindrical portion.

\* \* \* \* \*